United States Patent
Cha et al.

(10) Patent No.: US 11,304,930 B2
(45) Date of Patent: Apr. 19, 2022

(54) AMMONIUM SALTS OF 3-(3,5-DIBROMO-4-HYDROXYBENZYLIDEN)-5-INDO-1,3-DIHYDROINDOL-2-ONE AND USES THEREOF

(71) Applicant: Metagone Biotech Inc., Taipei (TW)

(72) Inventors: Tai-Lung Cha, Taipei (TW); Tai-Wei Ly, Taipei (TW); Yi-Ta Tsai, Taipei (TW); Sheng-Chieh Lin, Taipei (TW); Yun Yu, Taipei (TW)

(73) Assignee: Metagone Biotech Inc., Taipei (TW)

( * ) Notice: Subject to any disclaimer, the term of this patent is extended or adjusted under 35 U.S.C. 154(b) by 0 days.

(21) Appl. No.: 17/258,688

(22) PCT Filed: Jul. 24, 2019

(86) PCT No.: PCT/CN2019/097525
§ 371 (c)(1),
(2) Date: Jan. 7, 2021

(87) PCT Pub. No.: WO2020/029799
PCT Pub. Date: Feb. 13, 2020

(65) Prior Publication Data
US 2021/0283103 A1   Sep. 16, 2021

Related U.S. Application Data

(60) Provisional application No. 62/715,296, filed on Aug. 7, 2018.

(51) Int. Cl.
| C07D 209/34 | (2006.01) |
| A61K 31/404 | (2006.01) |
| A61K 31/44  | (2006.01) |

(52) U.S. Cl.
CPC ......... *A61K 31/404* (2013.01); *A61K 31/44* (2013.01); *C07D 209/34* (2013.01)

(58) Field of Classification Search
CPC .................................................. C07D 209/34
See application file for complete search history.

(56) References Cited

FOREIGN PATENT DOCUMENTS

WO   1999010325 A1   3/1999

OTHER PUBLICATIONS

Cancer and Metastasis Reviews (1998), 17(1), 91-106.*
Science (1999), vol. 286, 531-537.*
Cancer [online], [retrieved on Jul. 6, 2007]. Retrieved from the internet, URL http://www.nlm.nih.gov/medlineplus/cancer.html>.*

* cited by examiner

*Primary Examiner* — Shawquia Jackson
(74) *Attorney, Agent, or Firm* — NZ Carr Law Office PLLC

(57) ABSTRACT

Disclosed herein is a compound of formula (I), which is ammonium salt of GW5074,

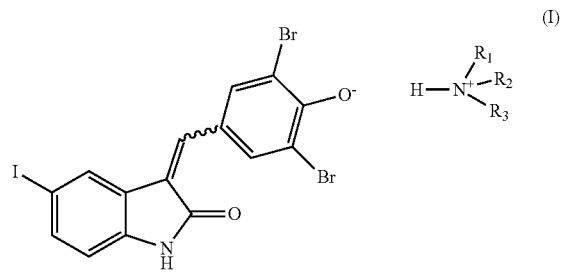

wherein $R_1$, $R_2$, and $R_3$ are independently hydrogen, alkyl, alkenyl, alkynyl, aryl, or heteroaryl; or $R_1$, $R_2$, $R_3$ and the nitrogen are taken together to form a 6-membered heterocyclyl; and the alkyl, the alkenyl, the alkynyl, the aryl, the heteroaryl, or the 6-membered heterocyclyl is optionally substituted with at least one substituent selected from the group consisting of, —OH, —NH$_2$, and —NR$^a$R$^b$, in which R$^a$ and R$^b$ are independently alkyl, aryl, or heteroaryl. Also disclosed herein is a pharmaceutical kit for the treatment of cancers. The pharmaceutical kit includes, a first formulation comprising a c-Raf inhibitor and a pharmaceutically acceptable carrier; and a second formulation comprising the compound of formula (I) and a pharmaceutically acceptable carrier. Also encompasses herein is a method of treating a subject having a cancer. The method comprises: (a) detecting whether the cancer cells of the subject has phosphorylation on serine 308 of death-associated protein kinase (DAPK); and (b) treating the subject based on the detection of the step (a) by, administering to the subject (i) an effective amount of a c-Raf inhibitor, and (ii) an effective amount of the compound of formula (I), when the phosphorylation on serine 308 of DAPK in the cancer cells is detected.

21 Claims, 1 Drawing Sheet

(A)
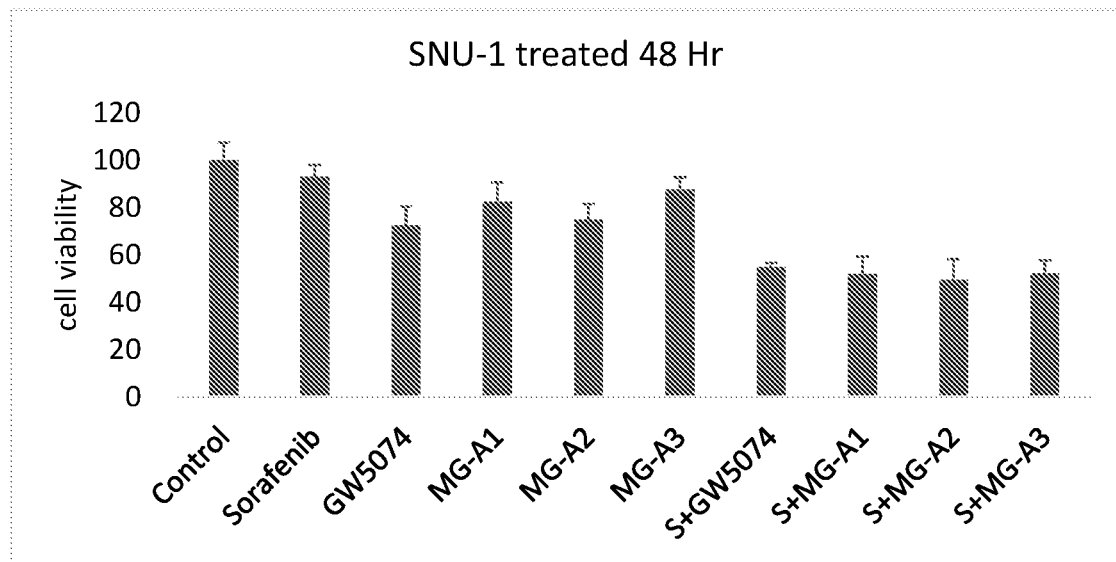
(B)
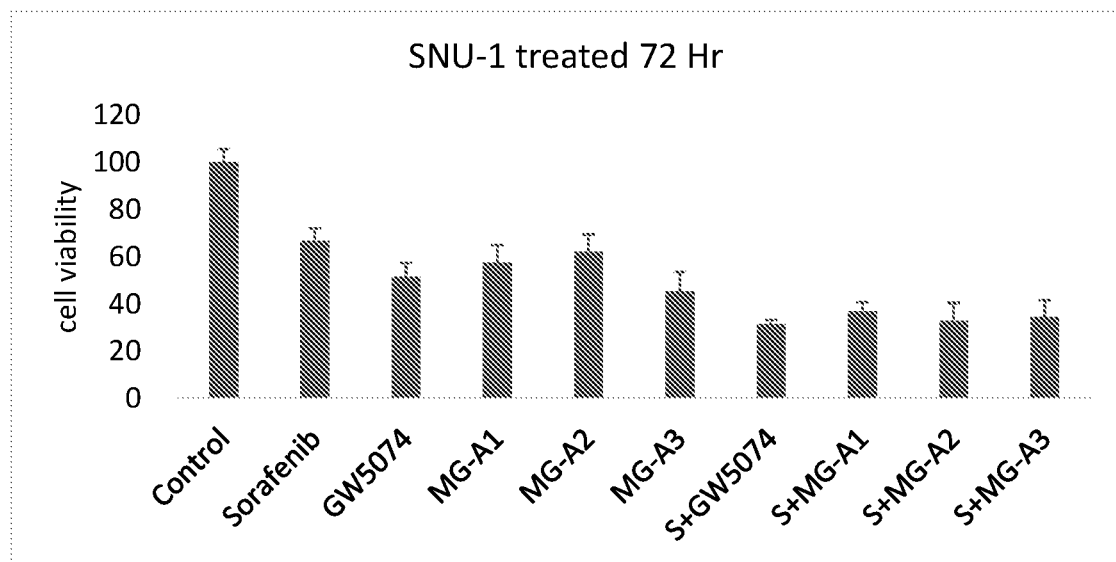

AMMONIUM SALTS OF 3-(3,5-DIBROMO-4-HYDROXYBENZYLIDEN)-5-INDO-1,3-DIHYDROINDOL-2-ONE AND USES THEREOF

CROSS-REFERENCE TO RELATED APPLICATION

This application claims priority to U.S. Provisional Patent Application Ser. No. 62/715,296, filed Aug. 7, 2018, the content of which is hereby incorporated by reference in its entirety.

BACKGROUND OF THE INVENTION

1. Field of the Invention

The present disclosure is generally directed to the ammonium salts of 3-(3,5-dibromo-4-hydroxybenzyliden)-5-iodo-1,3-duhydroindol-2-one (GW5074), and methods of treating cancers using the ammonium salts of GW5074.

2. Description of Related Art

Treating cancer patients with a c-Raf inhibitor (e.g., sorafenib) at an early stage may efficiently inhibit tumor size; yet it fails to eliminate tumors completely. Accordingly, an improved method of treating cancers by a combinational therapy of sorafenib and GW5074 has been suggested, provided that the cancers intended to be treated have phosphorylations on death-associated protein kinases (DAPKs) (see U.S. Pat. Nos. 9,273,034 and 9,393,234).

The present disclosure thus aims at providing a novel salt of GW5047 that may be used alone or in combination with a c-Raf inhibitor for the treatment of cancers. Surprisingly, the novel salts of GW5047 identified in the present disclosure exhibit improved pharmacokinetic (PK) properties as compared with those of non-salt forms.

SUMMARY

The following presents a simplified summary of the disclosure in order to provide a basic understanding to the reader. This summary is not an extensive overview of the disclosure and it does not identify key/critical elements of the present invention or delineate the scope of the present invention. Its sole purpose is to present some concepts disclosed herein in a simplified form as a prelude to the more detailed description that is presented later.

The present disclosure relates to novel ammonium salts of 3-(3,5-dibromo-4-hydroxybenzyliden)-5-iodo-1,3-duhydroindol-2-one (GW5074), and methods of treating cancers using the ammonium salts of GW5074, either alone or in combination with a c-Raf inhibitor (e.g., sorafenib).

More particularly, the present disclosure relates to a compound of formula (I), which is an ammonium salt of GW5074,

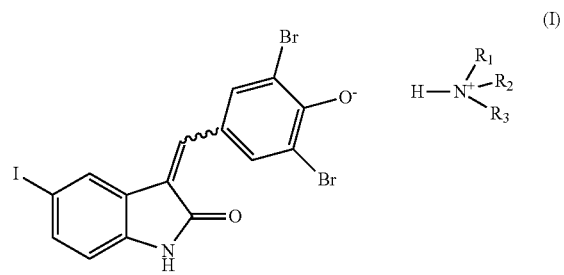

wherein, $R_1$, $R_2$, and $R_3$ are independently hydrogen, alkyl, alkenyl, alkynyl, aryl, or heteroaryl; or $R_1$, $R_2$, $R_3$ and the nitrogen are taken together to form a 6-membered heterocyclyl; and the alkyl, the alkenyl, the alkynyl, the aryl, the heteroaryl, or the 6-membered heterocyclyl is optionally substituted with at least one substituent selected from the group consisting of, —OH, —$NR^aR^b$ and a combination thereof, in which $R^a$ and $R^b$ are independently hydrogen, alkyl, aryl, or heteroaryl.

According to some preferred embodiments of the present disclosure, in the formula (I), $R_1$ and $R_2$ are independently hydrogen, and $R_3$ is tertiary-butyl substituted with at least one hydroxyl.

According to further preferred embodiments of the present disclosure, in the formula (I), $R_1$ and $R_2$ are independently hydrogen, and $R_3$ is ethyl optionally substituted with at least one amino or hydroxy.

According to further preferred embodiments of the present disclosure, in the formula (I), $R_1$, $R_2$, and $R_3$ are independently ethyl substituted with hydroxyl.

According to further preferred embodiments of the present disclosure, in the formula (I), $R_1$ is hydrogen, and $R_2$ is methyl, and $R_3$ is hexyl substituted with 6 hydroxy groups.

According to further preferred embodiments of the present disclosure, in the formula (I), $R_1$ is hydrogen, and $R_2$ is benzyl, and $R_3$ is ethyl substituted with —NH-benzyl.

According to further preferred embodiments of the present disclosure, in the formula (I), $R_1$, $R_2$, $R_3$ and the nitrogen are taken together to form piperazine, morpholine, or 4-(dimethylamino)pyridine.

The present disclosure also relates to a pharmaceutical kit useful for the treatment of a cancer. The kit includes, a first formulation comprising sorafenib and a pharmaceutically acceptable carrier; and a second formulation comprising the compound of formula (I) described above and the pharmaceutically acceptable carrier.

According to some preferred embodiments of the present disclosure, in the compound of formula (I) of the second formulation, $R_1$ and $R_2$ are independently hydrogen, and $R_3$ is tertiary-butyl substituted with at least one hydroxyl.

According to further preferred embodiments of the present disclosure, in the compound of formula (I) of the second formulation, $R_1$ and $R_2$ are independently hydrogen, and $R_3$ is ethyl optionally substituted with at least one amino or hydroxyl.

According to further preferred embodiments of the present disclosure, in the compound of formula (I) of the second formulation, $R_1$, $R_2$, and $R_3$ are independently ethyl substituted with hydroxyl.

According to further preferred embodiments of the present disclosure, in the compound of formula (I) of the second formulation, $R_1$ is hydrogen, and $R_2$ is methyl, and $R_3$ is hexyl substituted with 6 hydroxy groups.

According to further preferred embodiments of the present disclosure, in the compound of formula (I) of the second formulation, $R_1$ is hydrogen, and $R_2$ is benzyl, and $R_3$ is ethyl substituted with benzylamino.

According to further preferred embodiments of the present disclosure, in the compound of formula (I) of the second formulation, $R_1$, $R_2$, $R_3$ and the nitrogen are taken together to form piperazine, morpholine, or 4-(dimethylamino)pyridine.

Also encompasses in the present disclosure is a method for treating a subject having a cancer. The method includes steps of, (a) detecting whether the cancer cells of the subject has phosphorylation on serine 308 of death-associated protein kinase (DAPK); and (b) treating the subject based on the detection of the step (a) by administering to the subject (i) an effective amount of sorafenib, and (ii) an effective amount of the compound of formula (I), when the phosphorylation on serine 308 of DAPK in the cancer cells is detected.

According to some embodiments of the present disclosure, in the compound of formula (I), $R_1$ and $R_2$ are independently hydrogen, and $R_3$ is tertiary-butyl substituted with at least one hydroxyl.

According to further embodiments of the present disclosure, in the compound of formula (I), v.

Exemplary cancer treatable by the present method includes, but is not limited to, renal cell carcinoma, nephroblastoma, transitional cell carcinoma, prostate cancer, breast cancer, lung cancer, cervical carcinoma, oral cancer, glioma, urothelial cell carcinoma, and melanoma.

Many of the attendant features and advantages of the present disclosure will becomes better understood with reference to the following detailed description considered in connection with the accompanying drawings.

BRIEF DESCRIPTION OF THE DRAWINGS

The present description will be better understood from the following detailed description read in light of the accompanying drawings, where:

FIG. 1 are bar graphs depicting the viability of SUN-1 cells treated with the salts of GW5074 of Example 1 for (A) 48 hrs and (B) 72 hrs, respectively, in accordance with one embodiment of this invention.

DESCRIPTION

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

1. Definitions

For convenience, certain terms employed in the specification, examples and appended claims are collected here. Unless defined otherwise, all technical and scientific terms used herein have the same meaning as commonly understood by one of the ordinary skill in the art to which this invention belongs.

The term "alkyl" refers to a radical of a straight-chain or branched saturated hydrocarbon group having from 1 to 10 carbon atoms ("$C_{1-10}$ alkyl"). In some embodiments, an alkyl group has 1 to 6 carbon atoms ("$C_{1-6}$ alkyl"). Examples of $C_{1-6}$ alkyl groups include methyl ($C_1$), ethyl ($C_2$), propyl ($C_3$) (e.g., n-propyl, isopropyl), butyl ($C_4$) (e.g., n-butyl, tert-butyl, sec-butyl, iso-butyl), pentyl ($C_5$) (e.g., n-pentyl, 3-pentanyl, amyl, neopentyl, 3-methyl-2-butanyl, tertiary amyl), and hexyl ($C_6$) (e.g., n-hexyl). Additional examples of alkyl groups include n-heptyl ($C_7$), n-octyl ($C_8$), and the like. Unless otherwise specified, each instance of an alkyl group is independently optionally substituted (a "substituted alkyl" or an "unsubstituted alkyl") with one or more substituents (e.g., hydroxyl, or halogen such as Cl). In certain embodiments, the alkyl group is a substituted $C_2$ alkyl (e.g., —$CH_2CH_2OH$). In other embodiments, the alkyl is a substituted $C_4$ alkyl (e.g., a tert-butyl substituted with hydroxy).

The term "alkyenyl" refers to a radical of a straight-chain or branched hydrocarbon group having from 2 to 10 carbon atoms, one or more carbon-carbon double bonds, and no triple bonds ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently optionally substituted, i.e., unsubstituted (an "unsubstituted alkenyl") or substituted (a "substituted alkenyl") with one or more substituents. In certain embodiments, the alkenyl group is unsubstituted $C_{2-10}$ alkenyl. In certain embodiments, the alkenyl group is substituted $C_{2-10}$ alkenyl. In an alkenyl group, a C═C double bond for which the stereochemistry is not specified (e.g., —CH═CHCH$_3$ or

)

may be an (E)- or (Z)-double bond.

"Alkynyl" refers to a radical of a straight-chain or branched hydrocarbon group having from 2 to 10 carbon atoms, one or more carbon-carbon triple bonds, and optionally one or more double bonds ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently optionally substituted, i.e., unsubstituted (an "unsubstituted alkynyl") or substituted (a "substituted alkynyl") with one or more substituents. In certain embodiments, the alkynyl group is unsubstituted $C_{2-10}$ alkynyl. In certain embodiments, the alkynyl group is substituted $C_{2-10}$ alkynyl.

"Aryl" refers to a radical of a monocyclic or polycyclic (e.g., bicyclic or tricyclic) 4n+2 aromatic ring system (e.g., having 6, 10, or 14 pi electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently optionally substituted, i.e., unsubstituted (an "unsubstituted aryl") or substituted (a "substituted aryl") with one or more substituents. In certain embodiments, the aryl group is unsubstituted $C_{6-14}$ aryl. In certain embodiments, the aryl group is substituted $C_{6-14}$ aryl.

The term "heterocyclyl," "heterocycle," or "heterocyclic" refers to a radical of a 5- to 10-membered aromatic or non-aromatic ring system having ring carbon atoms and 1 to 4 ring heteroatoms, wherein each heteroatom is independently selected from nitrogen, oxygen, sulfur, boron, phosphorus, and silicon ("5-10 membered heterocyclyl"). A heterocyclyl group can be saturated or partially unsaturated. Heterocyclyl includes heteroaryl. Unless otherwise specified, each instance of heterocyclyl is independently optionally substituted, i.e., unsubstituted (an "unsubstituted heterocyclyl") or substituted (a "substituted heterocyclyl") with one or more substituents. In certain embodiments, the heterocyclyl group is unsubstituted 5-10 membered heterocyclyl. In certain embodiments, the heterocyclyl group is substituted 5-10 membered heterocyclyl. In some embodiments, a heterocyclyl group is a 5-8 membered ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur. Exemplary 5-membered heterocyclyl groups containing one heteroatom include, without limitation, tetrahydrofuranyl, dihydrofuranyl, tetrahydrothiophenyl, dihydrothiophenyl, furanyl, pyrrolidinyl, dihydropyrrolyl, thienyl and pyrrolyl-2,5-dione. Exemplary 5-membered heterocyclyl groups containing two heteroatoms include, without limitation, dioxolanyl, oxasulfuranyl, disulfuranyl, thiazolyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, opyranyl, dihydropyridinyl, pyridinyl, and thianyl. Exemplary 6-membered heterocyclyl groups containing two heteroatoms include, without limitation, piperazinyl, morpholinyl, dithianyl, dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl.

"Heteroaryl" refers to a radical of a 5-10 membered monocyclic or bicyclic 4n+2 aromatic ring system (e.g., having 6 or 10 pi electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). Heteroaryl bicyclic ring systems can include one or more heteroatoms in one or both rings. "Heteroaryl" includes ring systems wherein the heteroaryl ring is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl). In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, i.e., unsubstituted (an "unsubstituted heteroaryl") or substituted (a "substituted heteroaryl") with one or more substituents. In certain embodiments, the heteroaryl group is unsubstituted 5-14 membered heteroaryl. In certain embodiments, the heteroaryl group is substituted 5-14 membered heteroaryl. Exemplary 5-membered heteroaryl groups containing one heteroatom include, without limitation, pyrrolyl, furanyl, and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

An atom, moiety, or group described herein may be unsubstituted or substituted, as valency permits, unless otherwise provided expressly. The term "optionally substituted" refers to substituted or unsubstituted. A group is optionally substituted unless expressly provided otherwise. The term "optionally substituted" refers to being substituted or unsubstituted. In certain embodiments, alkyl, alkenyl, alkynyl, aryl, heterocyclyl and heteroaryl groups are optionally substituted (e.g., "substituted" or "unsubstituted" alkyl, "substituted" or "unsubstituted" alkenyl, "substituted" or "unsubstituted" alkynyl, "substituted" or "unsubstituted" aryl, "substituted" or "unsubstituted" heterocyclyl, or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present disclosure contemplates any and all such combinations in order to arrive at a stable compound. For purposes of this disclosure, heteroatoms such as nitrogen may have hydrogen substituents and/or any suitable substituent as described herein which satisfy the valences of the heteroatoms and results in the formation of a stable moiety. In certain embodiments, the substituent is a carbon atom substituent. In certain embodiments, the substituent is a nitrogen atom substituent. In certain embodiments, the substituent is an oxygen atom substituent. In certain embodiments, the substituent is a sulfur atom substituent.

As used in the present disclosure, the term "$C_{max}$" refers to the maximum concentration of an active compound or drug (e.g., GW5074) in the blood plasma, whereas the term "$T_{max}$" means the time to achieve the maximum plasma concentration of said active compound or drug. The term "$AUC_{0-t}$" refers to an area under the curve from zero to the last measured time point of a measurable drug concentration.

The singular forms "a", "and", and "the" are used herein to include plural referents unless the context clearly dictates otherwise. The term "about" as used herein generally means within 10%, 5%, 1%, or 0.5% of a given value or range. Alternatively, the term "about" means within an acceptable standard error of the mean when considered by one of ordinary skill in the art. Other than in the operating/working examples, or unless otherwise expressly specified, all of the numerical ranges, amounts, values and percentages such as those for quantities of materials, durations of times, temperatures, operating conditions, ratios of amounts, or reflection angles disclosed herein should be understood as modified in all instances by the term "about." Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques.

The term "treatment" as used herein are intended to mean obtaining a desired pharmacological and/or physiologic effect, e.g., reducing the size of a tumor in a subject. The effect may be prophylactic in terms of completely or partially preventing a disease or symptom thereof and/or therapeutic in terms of a partial or complete cure for a disease and/or adverse effect attributable to the disease. "Treatment" as used herein includes, but is not limited to, preventative (e.g., prophylactic), curative or palliative treatment of a disease in a mammal, particularly human; and includes: (1) preventative (e.g., prophylactic), curative or palliative treatment of a disease or condition (e.g., cancer) from occurring in an individual who may be pre-disposed to the disease but has not yet been diagnosed as having it; (2) inhibiting a disease (e.g., by suppressing proliferation of cancer cells); or (3) relieving a disease (e.g., reducing symptoms associated with the disease).

The term "administered", "administering" or "administration" are used interchangeably herein to refer a mode of delivery, including, without limitation, orally, intravenously, intramuscularly, intraperitoneally, intraarterially, intracranially, transmucosally (e.g., inhalation, and intranasally), or subcutaneously administering of an agent (e.g., a compound or a composition) of the present invention. In preferred embodiments, the ammonium salt of GW5074 is formulated into compositions that are suitable for oral administration.

The term "an effective amount" as used herein refers to an amount effective, at dosages, and for periods of time necessary, to achieve the desired result with respect to the treatment of a disease resulted from hyperglycemia. For example, in the treatment of a cancer, an agent (i.e., the ammonium salt of GW5074) which decrease, prevents, delays or suppresses or arrests any symptoms related to the cancer would be effective. An effective amount of an agent is not required to cure a disease or condition but will provide a treatment for a disease or condition such that the onset of the disease or condition is delayed, hindered or prevented, or the disease or condition symptoms are ameliorated. The specific effective or sufficient amount will vary with such factors as the particular condition being treated, the physical condition of the patient (e.g., the patient's body mass, age, or gender), the type of mammal or animal being treated, the duration of the treatment, the nature of concurrent therapy (if any), and the specific formulations employed and the like. Effective amount may be expressed, for example, as the total mass of the active agent (e.g., in grams, milligrams or micrograms) per day, or as the weight of the active agent per Kg of the body weight. The effective amount may be divided into one, two or more doses in a suitable form to be administered at one, two or more times throughout a designated time period. Further, persons having ordinary skills could calculate the human equivalent dose (HED) for the medicament (such as the compounds of the present disclosure) based on the doses determined from animal models set forth in the working examples of the present disclosure. For example, one may follow the guidance for industry published by US Food and Drug Administration (FDA) entitled "Estimating the Maximum Safe Starting Dose in Initial Clinical Trials for Therapeutics in Adult Healthy Volunteers" in estimating a maximum safe dosage for use in human subjects.

The term "subject" or "patient" is used interchangeably herein and is intended to mean a mammal including the human species that is treatable by the compound of the present invention. The term "mammal" refers to all members of the class Mammalia, including humans, primates, domestic and farm animals, such as rabbit, pig, sheep, and cattle; as well as zoo, sports or pet animals; and rodents, such as mouse and rat. Further, the term "subject" or "patient" intended to refer to both the male and female gender unless one gender is specifically indicated. Accordingly, the term "subject" or "patient" comprises any mammal which may benefit from the treatment method of the present disclosure. Examples of a "subject" or "patient" include, but are not limited to, a human, rat, mouse, guinea pig, monkey, pig, goat, cow, horse, dog, cat, bird and fowl. In a preferred embodiment, the subject is a human.

The term "carrier" as used herein means any inert substance (such as a powder or liquid) that forms a vehicle for the active agent. The carrier is generally safe, non-toxic, and in a broad sense, may also include any known substance in the pharmaceutical industry useful for preparing pharmaceutical compositions such as, fillers, diluents, agglutinants, binders, lubricating agents, glidants, stabilizer, colorants, wetting agents, disintegrants, and etc.

II. Ammonium Salts of GW5074

The present invention in general, relates to novel pharmaceutical salts of GW5074. As GW5047 is an acid or an electron donor, desired pharmaceutically acceptable salt of GW5047 may be prepared by treating GW5047 with an inorganic base (e.g., NaOH) or an organic base (e.g., primary, secondary or tertiary amine) to form a pharmaceutically acceptable salt. The present invention thus relates to novel ammonium salts of GW5047 having the structure of formula (I),

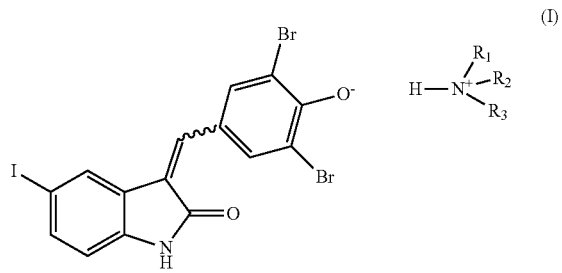

wherein,
$R_1$, $R_2$, and $R_3$ are independently hydrogen, alkyl, alkenyl, alkynyl, aryl, or heteroaryl; or $R_1$, $R_2$, $R_3$ and the nitrogen are taken together to form a 6-membered heterocyclyl; and the alkyl, the alkenyl, the alkynyl, the aryl, the heteroaryl, or the 6-membered heterocyclyl is optionally substituted with at least one substituent selected from the group consisting of, —OH, —NR$^a$R$^b$ and a combination thereof, in which R$^a$ and R$^b$ are independently hydrogen, alkyl, aryl, or heteroaryl.

The compound of formula (I) may be prepared by procedures described in the working examples. In general, the compound of formula (I) may be obtained by first suspending GW5047 in a polar aprotic solvent (e.g., acetone, dimethyl sulfoxide (DMSO), dimethylformamide (DMF), N-methyl-2-pyrrolidone (NMP), dichloromethane (DCM), tetrahydrofuran (THF) and the like) or a polar aprotic solvent (e.g., methanol, ethanol, 2-propanol, propanol and the like) before adding an amine, preferably, an amine substituted with hydroxyl, to the suspension to dissolve GW5047. The resulted mixture is vigorously stirred until the desired ammonium salt of GW5047 is formed. Examples of the amine suitable for the production of the present ammonium salts of GW5047 include, but are not limited to, ethanolamine (e.g., mono-, di-, and/or tri-ethanolamine), propanolamine (e.g., 1-amino-2-propanol), butanolamine (e.g., 1-amino-2-butanol, 1-amino-3-butanol, 1-amino-4-butanol, 2-amino-1-butanol, hydroxyl sec-butylamine, hydroxyl ter-butylamine), tris(hydroxymethyl)aminomethane, ethylenediamine, piperazine, morpholine, 4-(dimethylamino)pyridine, N,N'-dibenzylethyldiamine, N-methylglucamine, and the like. In one preferred embodiment, sufficient amount of triethanolamine is added to the GW5047 suspension to produce corresponding ammonium salt of GW5047. In another preferred embodiment, sufficient amount of hydroxyl tert-butylamine is added to the GW5047 suspension to produce corresponding ammonium salt of GW5047. In further embodiment, sufficient amount of piperazine is added to the GW5047 suspension to produce corresponding ammonium salt of GW5047. In still further embodiment, sufficient amount of 4-(dimethylamino)pyridine is added to the GW5047 suspension to produce corresponding ammonium salt of GW5047.

The ammonium salts of GW5047 of the present disclosure has a water solubility ranges from 0.01 mg/100 mL to 1,000 mg/100 mL, preferably from 0.1 mg/100 mL to 500 mg/100 mL, more preferably from 1 mg/100 mL to 300 mg/100 mL. In one embodiment, the triethanolammonium salt of GW5047 has a water solubility of 2.36 mg/100 mL. In another embodiment, the 4-(dimethylamino)pyridine salt of GW5047 has a water solubility of 1.5 mg/100 mL. In a further embodiment, the piperazine salt of GW5047 has a water solubility of 0.74 mg/100 mL. In another further embodiment, the ethylenediamine salt of GW5047 has a water solubility of 1.0 mg/100 mL. In another embodiment, the morpholine salt of GW5047 has a water solubility of 0.57 mg/100 mL. In a still further embodiment, the N-methylglucamine salt of GW5047 has a water solubility of 275 mg/100 mL.

In pharmacokinetic (PK) studies, $AUC_{0-t}$ of the active compound or drug is often used to assess the efficacy or the bioequivalence of the active compound/drug. In accordance with the present disclosure, the blood level of the active compound (i.e., GW5074) may be measured at 12, 24, 48, or 72 hours after the ingestion. In accordance with some embodiments of the present disclosure, the present ammonium salt of GW5047 may provide an average blood level $C_{max}$ of GW5047 in a range of about 6447 ng/mL during an average $T_{max}$ of about 0.5 hours, and an $AUC_{0-t}$ of GW5047 in a range of about 7936 ng·h/mL measured after 24 hours. In other embodiments, the present ammonium salt of GW5047 may provide an average blood level $C_{max}$ of GW5047 in a range of about 6844 ng/mL during an average $T_{max}$ of about 0.5 hours, and an $AUC_{0-t}$ of GW5047 in a range of about 8259 ng·h/mL measured after 24 hours.

III. Pharmaceutical Kits

In particular embodiments of the present disclosure, the compound of formula (I) or the ammonium salts of GW5047 described above are used alone or in combination with a c-Raf inhibitor (e.g., sorafenib) to treat cancers, particularly cancer cells that have phosphorylation on serine 308 of death-associated protein kinase (DAPK).

In accordance with certain embodiments of the present disclosure, the compound of formula (I) alone may suppress the proliferation of gastric cancer cells, and may act synergistically with a known c-Raf inhibitor (e.g., sorafenib), in reducing the number of proliferated gastric cancer cells. Accordingly, the compound of formula (I) may be used as an add-on medication with any known c-Raf inhibitor for the treatment of cancers, provided that the cancer has phosphorylation on serine 308 of DAPK.

Accordingly, the present disclosure also relates to a pharmaceutical kit useful for the treatment of a cancer. The kit includes: a first formulation comprising sorafenib and a pharmaceutically acceptable carrier; and a second formulation comprising the compound of formula (I) described above and the pharmaceutically acceptable carrier.

According to some preferred embodiments of the present disclosure, in the compound of formula (I) of the second formulation, $R_1$ and $R_2$ are independently hydrogen, and $R_3$ is ethyl optionally substituted with at least one amino or hydroxyl.

According to further preferred embodiments of the present disclosure, in the compound of formula (I) of the second formulation, $R_1$, $R_2$, and $R_3$ are independently ethyl substituted with hydroxyl.

According to further preferred embodiments of the present disclosure, in the compound of formula (I) of the second formulation, $R_1$ is hydrogen, and $R_2$ is methyl, and $R_3$ is hexyl substituted with 6 hydroxy groups (or 1-desoxysorbitol).

According to further preferred embodiments of the present disclosure, in the compound of formula (I) of the second formulation, $R_1$ is hydrogen, and $R_2$ is benzyl, and $R_3$ is ethyl substituted with —NH-benzyl.

According to further preferred embodiments of the present disclosure, in the compound of formula (I) of the second formulation, $R_1$, $R_2$, $R_3$ and the nitrogen are taken together to form piperazine, morpholine, or 4-(dimethylamino)pyridine.

The first and second formulations of the present disclosure are typically provided in dosage forms suitable for administration to a subject by any desired route. One of skill in the art is familiar with various dosage forms that are suitable for use in the present invention. The most suitable route in any given case will depend on the nature and severity of the disease being treated and/or managed. For example, the formulations may be formulated for administration orally, intraveneously, intramuscularly, intraperitoneally, intraarterially, intracranially, transmucosally (e.g., inhalation, buccal, and intranasally), or subcutaneously. Preferably, the formulations are administered orally. The dosage forms of the formulations suitable for oral administration includes, for example, tablets, pills, granules, powders, solutions, suspensions, syrups or capsules. As a method of producing solid dosage form such as a tablet, a pill, granule or powder, it can be formed by conventional techniques using a pharmaceutically acceptable carrier such as excipient, binder, or disintegrant and etc. The solid dosage form for oral administration may optionally be scored or prepared with coating and shells, such as entering coatings, and coatings for modifying the rate of release. Further, any of the solid dosage form may be encapsulated in soft and hard gelatin capsules using any of the excipients known in the art.

The compound of formula (I) (or the ammonium salts of GW5047) or the c-Raf inhibitor may also be formulated into a liquid dosage form for oral administration. Suitable formulation include emulsion, solutions, suspension or syrup, it can be produced by conventional techniques using diluents commonly used in the art, such as water, glycerol esters, alcohols, vegetable oils, and etc. The liquid formulation may optionally include adjuvants such as wetting agents, emulsifying agents, and suspending agents, sweetening, flavoring, coloring, and preservative agents. The liquid formulation may also be filled into soft gelatin capsules. For example, the liquid may include a solution, suspension, emulsion, precipitate, or any other desired liquid media carrying the ammonium salts of GW5047 or the c-Raf inhibitor. The liquid may be designed to improve the solubility of the ammonium salts of GW5047 or the c-Raf inhibitor upon release, or may be designed to form a drug-containing emulsion or dispersed phase upon release. Examples of such techniques are well known in the related art. Soft gelatin capsules may be coated, as desired, with a functional coating, such as to delay the release of the drug.

In the case of parenteral administration, the ammonium salts of GW5047 or the c-Raf inhibitor may be formulated into injectable forms for intravenous, subcutaneous or intramuscular administration. An injection can be prepared by dissolving the ammonium salts of GW5047 or the c-Raf inhibitor in water soluble solution such as physiological saline, or water insoluble solution consisting of organic esters such as propylene glycol, polyethylene glycol, or vegetable oils (e.g., sesame oil).

In the case of transdermal administration, for example, a dosage form as an ointment or a cream can be employed. The ointment can be produced by mixing the ammonium salts of GW5047 or the c-Raf inhibitor with fats or oils and etc; and the cream can be produced by mixing the ammonium salts of GW5047 or the c-Raf inhibitor with emulsifiers. The transdermal formulation may be in a form of a liquid or a powdery formulation. In a liquid formulation, water, salt solution, phosphate buffer, acetate buffer and etc may be used as a base; it may also contain surfactants, antioxidants, stabilizers, preservatives or tackifiers. In a powdery formulation, it may contain water-absorbing materials such as water-soluble polyacrylates, cellulose low-alkyl esters, polyethylene glycol polyvinyl pyrrolidone, amylase and etc, and non-water absorbing materials such as cellulose, starches, gums, vegetable oils or cross-linked polymers. Further, antioxidants, colorants, preservatives may be added to the powdery formulation. The liquid or powdery formulation may be administered by use of a spray apparatus.

In the case of rectal administration, it may be in the form of suppository using a gelatin soft capsule.

In case of inhalation through nose or mouth, a solution or suspension containing the ammonium salts of GW5047 (or the c-Raf inhibitor) and a pharmaceutical excipient generally accepted for this purpose is inhaled through an inhalant aerosol spray. Alternatively, the ammonium salts of GW5047 or the c-Raf inhibitor in the form of a powder may be administered through inhalator that allows direct contact of the powder with the lung. To these formulations, if necessary, pharmaceutical acceptable carriers such as isotonic agents, preservatives, dispersions, or stabilizers may be added. Further, if necessary, these formulations may be sterilized by filtration, or by treatment with heat or irradiation.

In general, the formulation comprising the ammonium salts of GW5047 or the c-Raf inhibitor is administered to the subject in single or divided doses 2, 3, 4, 5, 6 or more times each day. Alternatively, the dose may be delivered once every 2, 3, 4, 5, 6 or more days. In one preferred embodiment, the formulation is administered once per day. In another embodiment, the formulation is administered twice per day.

IV. Methods of Treatment

Also encompasses in the present disclosure is a method for treating a subject having a cancer. The method includes steps of, (a) detecting whether the cancer cells of the subject has phosphorylation on serine 308 of death-associated protein kinase (DAPK); and (b) treating the subject based on the detection of the step (a) by administering to the subject (i) an effective amount of sorafenib, and (ii) an effective amount of the compound of formula (I), when the phosphorylation on serine 308 of DAPK in the cancer cells is detected.

The compound of formula (I) (or the ammonium salts of GW5047) preferably is prepared in accordance with the method set forth in working examples of this disclosure.

According to embodiments of the present disclosure, the compound of formula (I) has the structure of,

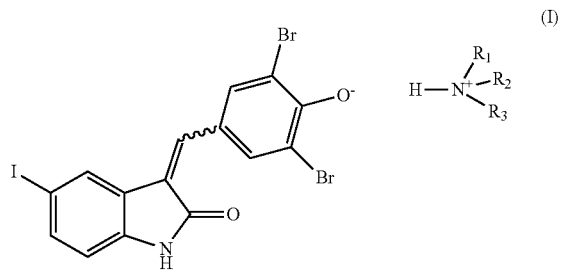

wherein, $R_1$, $R_2$, and $R_3$ are independently hydrogen, alkyl, alkenyl, alkynyl, aryl, or heteroaryl; or $R_1$, $R_2$, $R_3$ and the nitrogen are taken together to form a 6-membered heterocyclyl; and the alkyl, the alkenyl, the alkynyl, the aryl, the heteroaryl, or the 6-membered heterocyclyl is optionally substituted with at least one substituent selected from the group consisting of, —OH, —NR$^a$R$^b$ and a combination thereof, in which R$^a$ and R$^b$ are independently hydrogen, alkyl, aryl, or heteroaryl.

According to one preferred embodiment of the present disclosure, in the formula (I), $R_1$ and $R_2$ are independently hydrogen, and $R_3$ is ethyl optionally substituted with at least one amino or hydroxyl.

According to further preferred embodiments of the present disclosure, in the compound of formula (I) of the second formulation, $R_1$, $R_2$, and $R_3$ are independently ethyl substituted with hydroxyl.

According to further preferred embodiments of the present disclosure, in the compound of formula (I) of the second formulation, $R_1$ is hydrogen, and $R_2$ is methyl, and $R_3$ is hexyl substituted with 6 hydroxy groups.

According to further preferred embodiments of the present disclosure, in the compound of formula (I) of the second formulation, $R_1$ is hydrogen, and $R_2$ is benzyl, and $R_3$ is ethyl substituted with —NH-benzyl.

According to further preferred embodiments of the present disclosure, in the compound of formula (I) of the second formulation, $R_1$, $R_2$, $R_3$ and the nitrogen are taken together to form piperazine, morpholine, or 4-(dimethylamino)pyridine.

According to preferred embodiments, the compound of formula (I) is administered with the c-Raf inhibitor, to suppress the growth of cancer cells in the subject, provided that the cancer cells have phosphorylation on Ser 308 of DAPK. Any known c-Raf inhibitor may be used. Preferably, the c-Raf inhibitor is sorafenib, ZM336372, TK-632, NVP-BHG712, or a combination thereof.

Exemplary cancer treatable by the present method includes, but is not limited to, renal cell carcinoma, nephroblastoma, transitional cell carcinoma, prostate cancer, breast cancer, lung cancer, cervical carcinoma, oral cancer, glioma, urothelial cell carcinoma, and melanoma.

According to embodiments of the present disclosure, the compound of formula (I) and the c-Raf inhibitor may be respectively administered to the subject in need of such treatment in the effective dose amount. In certain embodiments, the amount administered is in the range of 0.01 to 100 mg/Kg, such as 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 and 100 mg/Kg; preferably, the compound of formula (I) and the c-Raf inhibitor are respectively administered in the amount from about 0.5 to 50 mg/Kg, such as 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 mg/Kg; more preferably, the compound of formula (I) and the c-Raf inhibitor are respectively administered in the amount from about 1 to 20 mg/Kg, such as 1, 2, 3, 4, 5, 6, 7, 8, 9, 10, 11, 12, 13, 14, 15, 16, 17, 18, 19 and 20 mg/Kg. According to embodiments of the present disclosure, the compound of formula (I) and the c-Raf inhibitor may be administered independently via any suitable route, which includes, but is not limited to, oral, intraveneous, intramuscular, intraperitoneal, intraarterial, intracranial, and subcutaneous route. In preferred embodiment, an effective amount of the compound of formula (I) or the c-Raf inhibitor is administered orally to the subject in need thereof.

The present invention will now be described in further detail with reference to the following examples. However, it should be understood that the present invention is not limited to the specified examples.

EXAMPLES

Materials and Methods
Cell Lines and Cell Culture
Gastric cancer cell line SUN-1 was purchased from the American Type Culture Collection (ATCC; Manassas, Va., USA) and were maintained in Roswell Park Memorial Institute-1640 (RPMI-1640) supplemented with 1.5 g/L sodium bicarbonate, 10% fetal bovine serum (FBS), 1.0% antibiotic-antimycotic, L-glutamine ($2.0\times10^{-3}$ M), and 1.0% nonessential amino acids.

Dissolution

A size 0 gelatin capsule was filled with the test compound (20 mg) and PROSOLV® SMCC 90 (100 mg) and capped. The filled capsule was shaken vigorously to thoroughly mix the contents. Then, the capsule was dropped into a 50 mL conical vial containing 3% SLS buffer (40 mL). The conical vial was then fixed, at room temperature, to a rotor angled at ca. 60 degrees from horizontal with the rotation speed set at 50 rpm. At each sampling time point, the rotation was stopped, 0.5 mL of media was removed, the vial re-capped, and rotation restarted. The sampled media was centrifuged at 3,000 rpm for 2 minutes, and 50 µL of the mother liquor was aliquoted and diluted with 100 µL of IN NaOH. The absorbance at 355 nm of the diluted sample was measured with a plate reader.

Animals

B6 mice about 6-8 weeks of age (National laboratory animal center, Taipei, Taiwan) were used in the present study. All animals were maintained in the animal facility with controlled temperature (20-24° C.), humidity (50-80%) and a 12 h/12 h light/dark cycle (light on at 7:00 a.m.) with food and water provided ad libitum. Experimental procedures for handling animals complied with relevant, regulations set forth in "Guide for the Care and Use of Laboratory Animals: Eighth Edition" (National Academies Press, Washington, D.C., 2011) in AAALAC-accredited laboratory animal facility.

Cell Viability Assay

MTS cell proliferation assay kit (Abcam, Cambridge, UK) was used to evaluate cell viability. Briefly, SNU-1 cells were seeded in each well of a 96-well plate at the density of 8,000 cells/well and incubated overnight at 37° C. Cells were then treated with a test drug for 48 or 72 h at 37° C. Then, 20 µl MTS/well was added and incubated for 3 h at 37° C. Cell viability was measured by absorbance at 490 nm in a microplate reader.

Statistics

Results were expressed as the mean±standard error of the mean (SEM). Unpaired student's t-test or 1-way ANOVA was used for statistical comparisons between substance-treated and vehicle-treated groups. Differences are considered significant at $P<0.05$, vs vehicle control.

Comparative Example 1 Preparation of Potassium or Sodium Salts of GW5074

1.1 Potassium Salts of GW5074

The potassium salts of GW5074 were prepared in accordance with the general procedures described in Example 1.1 except KOH was added to the GW5074 suspension.

$^1$H NMR (400 MHz, D$_6$-DMSO) (δ10.42 (app, d, 1H), 8.74 (2H, s), 7.98-7.81 (app, t, 2H), 7.53-7.31 (2H, m), 6.64 (1H, 2×d))

Melting point: 293° C.

Solubility: 0.5 mg/100 mL 1.2 Sodium Salts of GW5074 (MG-A1)

The sodium salts of GW5074 were prepared in accordance with the general procedures described in Example 1.1 except NaOH was added to the GW5074 suspension.

$^1$H NMR (400 MHz, D$_6$-DMSO) (δ10.34 (app, d, 1H), 8.742 (1H, s), 8.05-7.76 (app, t, 2H), 7.48-7.27 (2H, m), 6.63 (1H, 2×d))

Melting point: 327° C.

Solubility: 0.5 mg/100 mL

Example 1 Preparation of the Ammonium Salt of GW5074

1.1 2-Amino-2-Methylpropylamine Salt of GW5075 (MG-A2)

To a suspension of GW5074 (2.05 g) in acetone (20 mL) at room temperature was added 2-amino-2-methylpropanol (0.41 mL; 1.1 eq). The resulting clear red solution was stirred at room temperature for 16 hours and then treated with diisopropylether (60 mL). The resulting orange suspension was stirred vigorously for 30 minutes and then filtered in vacuo. The filter cake was rinsed with copious amounts of diisopropylether and dried under vacuum at room temperature to give the desired product as a bright orange solid (2.03 g).

$^1$H NMR (400 MHz, D$_6$-DMSO) (δ10.33 (1H, s), 8.72 (2H, s), 7.85 (1H, s), 7.64 (2H, s), 7.48 (1H, s), 7.28 (1H, d), 6.57 (1H, t), 5.48 (1H, s), 2.08 (2H, d), 1.11 (6H, m))

Melting point: 247° C.

Solubility: 0.19 mg/100 mL 1.2 Triethanolamine Salt of GW5075 (MG-A3)

The ammonium salts of GW5074 were prepared in accordance with the general procedures described in Example 1.1 except triethanolamine was added to the GW5074 suspension.

$^1$H NMR (400 MHz, D$_6$-DMSO) (δ10.42 (1H, s), 8.73 (2H, s), 7.87 (1H, s), 7.53 (1H, s), 7.32 (1H, q), 6.32 (1H, d), 5.01 (3H, s), 3.32 (6H, s), 3.08 (6H, s))

Melting point: 103° C.

Solubility: 2.36 mg/100 mL 1.3 Diethylamine Salt of GW5075

The ammonium salts of GW5074 were prepared in accordance with the general procedures described in Example 1.1 except diethylamine was added to the GW5074 suspension.

$^1$H NMR (400 MHz, D$_6$-DMSO) (δ10.35 (1H, s), 8.73 (2H, s), 8.25 (2H, s), 7.85 (1H, d), 7.49 (1H, s), 7.29 (1H, q), 6.58 (1H, d), 2.92 (4H, m), 1.15 (6H, t))

Melting point: 250° C.

Solubility: 0.12 mg/100 mL 1.4 N-Methylglucamine Salt of GW5075

The ammonium salts of GW5074 were prepared in accordance with the general procedures described in Example 1.1 except N-methylglucamine was added to the GW5074 suspension.

$^1$H NMR (400 MHz, D$_6$-DMSO) (δ10.38 (1H, s), 8.73 (1H, s), 8.05-7.85 (1H, 2×s), 7.76 (1H, s), 7.49-7.41 (1H, m), 7.33 (1H, t), 6.68 (1H, q), 3.80 (2H, m), 2.87 (5H, m))

Melting point: 175° C.

Solubility: 275 mg/100 mL 1.5 N, N'-Dibenzylethylenediamine Salt of GW5075

The ammonium salts of GW5074 were prepared in accordance with the general procedures described in Example 1.1 except N,N'-dibenzylethylenediamine was added to the GW5074 suspension.

$^1$H NMR (400 MHz, D$_6$-DMSO) (δ10.53 (1H, s), 8.76 (2H, s), 7.59 (app, d, 1H), 7.62 (1H, s), 7.38 (11H, m), 6.62 (1H, d), 3.99 (4H, s), 2.96 (4H, s))

Melting point: 215° C.

Solubility: <0.02 mg/100 mL 1.6 Piperazine Salt of GW5075

The ammonium salts of GW5074 were prepared in accordance with the general procedures described in Example 1.1 except piperazine was added to the GW5074 suspension.

$^1$H NMR (400 MHz, D$_6$-DMSO) (δ10.41 (1H, s), 8.05 (2H, s), 7.815 (2H, 2×s), 7.40 (2H, 4×s), 6.66 (1H, 2×d), 2.88 (8H, s))

Melting point: 244° C.

Solubility: 0.74 mg/100 mL 1.7 4-(Dimethylamino)Pyridine Salt of GW5075

The ammonium salts of GW5074 were prepared in accordance with the general procedures described in Example 1.1 except 4-(dimethylamino)pyridine was added to the GW5074 suspension.

$^1$H NMR (400 MHz, D$_6$-DMSO) (δ10.40 (1H, s), 8.74 (2H, s), 8.19 (2H, d), 7.87 (app, t, 2H), 7.53 (1H, s), 7.31 (1H, d), 6.90 (2H, d), 6.59 (1H, d), 3.13 (6H, s)

Melting point: 242° C.
Solubility: 1.5 mg/100 mL 1.8 Morpholine Salt of GW5075

The ammonium salts of GW5074 were prepared in accordance with the general procedures described in Example 1.1 except morpholine was added to the GW5074 suspension.

$^1$H NMR (400 MHz, D$_6$-DMSO) (δ10.40 (app, d, 1H), 8.02 (1H, s), 7.82 (app, d, 1H), 7.75-7.35 (2H, m), 6.63 (1H, 2×d), 3.74 (4H, q), 2.49 (4H, m))

Melting point: 266° C.
Solubility: 0.57 mg/100 mL 1.9 Tris(Hydroxymethyl)Aminomethane Salt of GW5075

The ammonium salts of GW5074 were prepared in accordance with the general procedures described in Example 1.1 except Tris-base (Tris(hydroxymethyl)aminomethane) was added to the GW5074 suspension.

$^1$H NMR (400 MHz, D$_6$-DMSO) (δ10.35 (1H, s), 8.72 (1H, s), 8.05-7.76 (app, t, 2H), 7.29 (2H, m), 6.62 (1H, q), 5.71 (2H, s), 4.87 (3H, s), 3.35 (6H, d))

Melting point: 142° C.
Solubility: <0.02 mg/100 mL 1.10 Ethylenediamine salt of GW5075

The ammonium salts of GW5074 were prepared in accordance with the general procedures described in Example 1.1 except ethylenediamine was added to the GW5074 suspension.

$^1$H NMR (400 MHz, D$_6$-DMSO) (δ60.37 (1H, s), 8.73 (2H, s), 7.85 (1H, s), 7.50 (1H, s), 7.29 (1H, q), 6.59 (1H, 2×d), 3.36 (4H, s))

Melting point: 185° C.
Solubility: 1 mg/100 mL

Example 2 Characterization of the Ammonium Salts of GW5074 of Example 1

To validate the bioactivity of the ammonium salts of GW5074 of Example 1, their effects on cell proliferation with or without the addition of another cell proliferation inhibitor-sorafenib, were investigated using MTS cell proliferation assay kit in accordance with the manufacturer's protocols. Results are illustrated FIGS. 1A and 1B.

As depicted in FIG. 1A, treating gastric cancer cells (SUN-1 cells) with sorafenib (5 mM), GW5074 (10 mM), MG-A1 (sodium salt of GW5074)(10 mM), MG-A2 (10 mM), or MG-A3 (10 mM) for 48 hrs resulted in minor suppression (about 10-20% inhibition compared to the control) on the growth of SUN-1 cells; however, if SUN-1 cells were treated with a combination of drugs (sorafenib in combination with GW5074, MG-A1, MG-A2, or MG-A3), then the degree of suppression would go up to about 55-60% inhibition as compared to that of the control.

The growth inhibition was more significant when cells were treated with the test substance(s) for 72 hrs. As depicted in FIG. 1B, about 40-60% growth inhibition was achieved by sorafenib, GW5074, MG-A1, MG-A2, or MG-A3 alone; and about 70% growth inhibition was achieved when cells were treated with a combination of drugs (i.e., sorafenib in combination with GW5074, MG-A1, MG-A2, or MG-A3).

Example 3 Pilot Pharmacokinetic (PK) Study of the Ammonium Salt of GW5074 of Example 1

Pilot PK studies were carried out in mice. Each mice received a single-dose medication, either positive control formulation (GW5074) or the respective ammonium salts of examples 1.1 and 1.2; PK properties of GW5074 in each test subjects were then analyzed and recorded.

Mice were fasting for 8 hrs before dosing. They were randomly allocated to three groups, which were GW5074 group, MG-A2 (i.e., the ammonium salt of GW5074 of Example 1.1) group, and MG-A3 (i.e., the ammonium salt of GW5074 of Example 1.2) group. Each doses (40 mg/Kg) was prepared by dissolving the active compound (GW5074 or the GW5074 salt) in a solution composed of SOLUTOL™ (Sigma-Aldrich, St. Louis, Mo., USA), water and ethanol in a volume ratio of 4:1:5. Blood samples were drawn from the tail vein at pre-designated time points. Each samples were extracted with 80% ethanol for 30 minutes and individually filtered through a 0.22 μm PVDF filter, then were subjected to HPLC-MS/MS.

PK properties including maximal plasma concentration ($C_{max}$), time to reach the peak concentration ($T_{max}$), time required for the plasma drug concentration to decrease by one half ($T_{1/2}$), and the area under the plasma concentration verses time curve from zero to the last measured time point ($AUC_{0-t}$) were assessed immediately before (0 hour) and at 0.5, 1, 2, 4, 8, and 24 hours after drug administration. The thus-obtained PK properties of GW5074 of each groups are summarized in Table 1.

TABLE 1

| PK Properties of GW5074, MG-A2, and MG-A3 in mice | | | |
|---|---|---|---|
| Compound name | GW 5074 | MG-A2 | MG-A3 |
| $T_{1/2}$ (hr) | 3.719 | 4.855 | 4.364 |
| $C_{max}$ (ng/mL) | 4905.2 | 6447.7 | 6844.6 |
| $T_{max}$ (hr) | 0.5 | 0.5 | 0.5 |
| $AUC_{0-t}$ (ng*h/mL) | 6127.9 | 7936.2 | 8258.7 |

Results from Table 1 revealed that the time required for the ammonium salt of GW5074 (either MG-A2 or MG-A3) to reach the peak concentration was same as that of the control GW5074, however, the maximum concentration ($C_{max}$) was higher for the MG-A2 or MG-A3 salt form, accordingly, it took much longer for the plasma drug concentration to decrease by one half, suggesting the ammonium salt of GW5074 (either MG-A2 or MG-A3) was relatively more stable or less prone to degradation in vivo, as compared to the control GW5074.

It will be understood that the above description of embodiments is given by way of example only and that various modifications may be made by those with ordinary skill in the art. The above specification, examples, and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

What is claimed is:

1. A compound of formula (I),

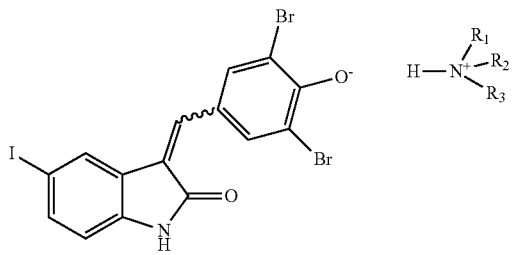

wherein,
R₁, R₂, and R₃ are independently hydrogen, alkyl, alkenyl, alkynyl, aryl, or heteroaryl; or
R₁, R₂, R₃ and the nitrogen are taken together to form a 6-membered heterocyclyl; and
the alkyl, the alkenyl, the alkynyl, the aryl, the heteroaryl, or the 6-membered heterocyclyl is optionally substituted with at least one substituent selected from the group consisting of, —OH, —N$^a$R$^b$ and a combination thereof, in which R$^a$ and R$^b$ are independently hydrogen, alkyl, aryl, or heteroaryl.

2. The compound of claim 1, wherein in the formula (I), R₁ and R₂ are independently hydrogen, and R₃ is tertiary-butyl substituted with at least one hydroxyl.

3. The compound of claim 1, wherein in the formula (I), R₁ and R₂ are independently hydrogen, and R₃ is ethyl optionally substituted with at least one amino or hydroxy.

4. The compound of claim 1, wherein in the formula (I), R₁, R₂, and R₃ are independently ethyl substituted with hydroxyl.

5. The compound of claim 1, wherein in the formula (I), R₁ is hydrogen, and R₂ is methyl, and R₃ is hexyl substituted with 6 hydroxy groups.

6. The compound of claim 1, wherein in the formula (I), R₁ is hydrogen, and R₂ is benzyl, and R₃ is ethyl substituted with NH-benzyl.

7. The compound of claim 1, wherein in the formula (I), R₁, R₂, R₃ and the nitrogen are taken together to form piperazine, morpholine, or 4-(dimethylamino)pyridine.

8. A pharmaceutical kit comprising:
a first formulation comprising sorafenib and a pharmaceutically acceptable carrier; and
a second formulation comprising the compound of claim 1 and a pharmaceutically acceptable carrier.

9. The pharmaceutical kit of claim 8, wherein in the compound of formula (I) of the second formulation, R₁ and R₂ are independently hydrogen, and R₃ is tertiary-butyl substituted with at least one hydroxyl.

10. The pharmaceutical kit of claim 8, wherein in the compound of formula (I) of the second formulation, R₁ and R₂ are independently hydrogen, and R₃ is ethyl optionally substituted with at least one amino or hydroxy.

11. The pharmaceutical kit of claim 8, wherein in the compound of formula (I) of the second formulation, R₁, R₂, and R₃ are independently ethyl substituted with hydroxyl.

12. The pharmaceutical kit of claim 8, wherein in the compound of formula (I) of the second formulation, R₁ is hydrogen, and R₂ is methyl, and R₃ is R₃ is hexyl substituted with 6 hydroxy groups.

13. The pharmaceutical kit of claim 8, wherein in the compound of formula (I) of the second formulation, R₁ is hydrogen, and R₂ is benzyl, and R₃ is ethyl substituted with NH-benzyl.

14. The pharmaceutical kit of claim 8, wherein in the compound of formula (I) of the second formulation, R₁, R₂, R₃ and the nitrogen are taken together to form piperazine, morpholine, or 4-(dimethylamino)pyridine.

15. A method for treating a subject having a gastric cancer comprising:
(a) detecting whether the gastric cancer cells of the subject has phosphorylation on serine 308 of death-associated protein kinase (DAPK); and
(b) treating the subject based on the detection of the step (a) by,
administering to the subject (i) an effective amount of sorafenib, and (ii) an effective amount of the compound of claim 1, when the phosphorylation on serine 308 of DAPK in the gastric cancer cells is detected.

16. The method of claim 15, wherein in the compound of formula (I), R₁ and R₂ are independently hydrogen, and R₃ is tertiary-butyl substituted with at least one hydroxyl.

17. The method of claim 15, wherein in the compound of formula (I) of the second formulation, R₁ and R₂ are independently hydrogen, and R₃ is ethyl optionally substituted with at least one amino or hydroxy.

18. The method of claim 15, wherein in the compound of formula (I) of the second formulation, R₁, R₂, and R₃ are independently ethyl substituted with hydroxyl.

19. The method of claim 15, wherein in the compound of formula (I) of the second formulation, R₁ is hydrogen, and R₂ is methyl, and R₃ is R₃ is hexyl substituted with 6 hydroxy groups.

20. The method of claim 15, wherein in the compound of formula (I) of the second formulation, R₁ is hydrogen, and R₂ is benzyl, and R₃ is ethyl substituted with —NH-benzyl.

21. The method of claim 15, wherein in the compound of formula (I) of the second formulation, R₁, R₂, R₃ and the nitrogen are taken together to form piperazine, morpholine, or 4-(dimethylamino)pyridine.

* * * * *